June 19, 1956 M. L. WHISLER Plant Pat. 1,487
ROSE PLANT
Filed Oct. 21, 1955
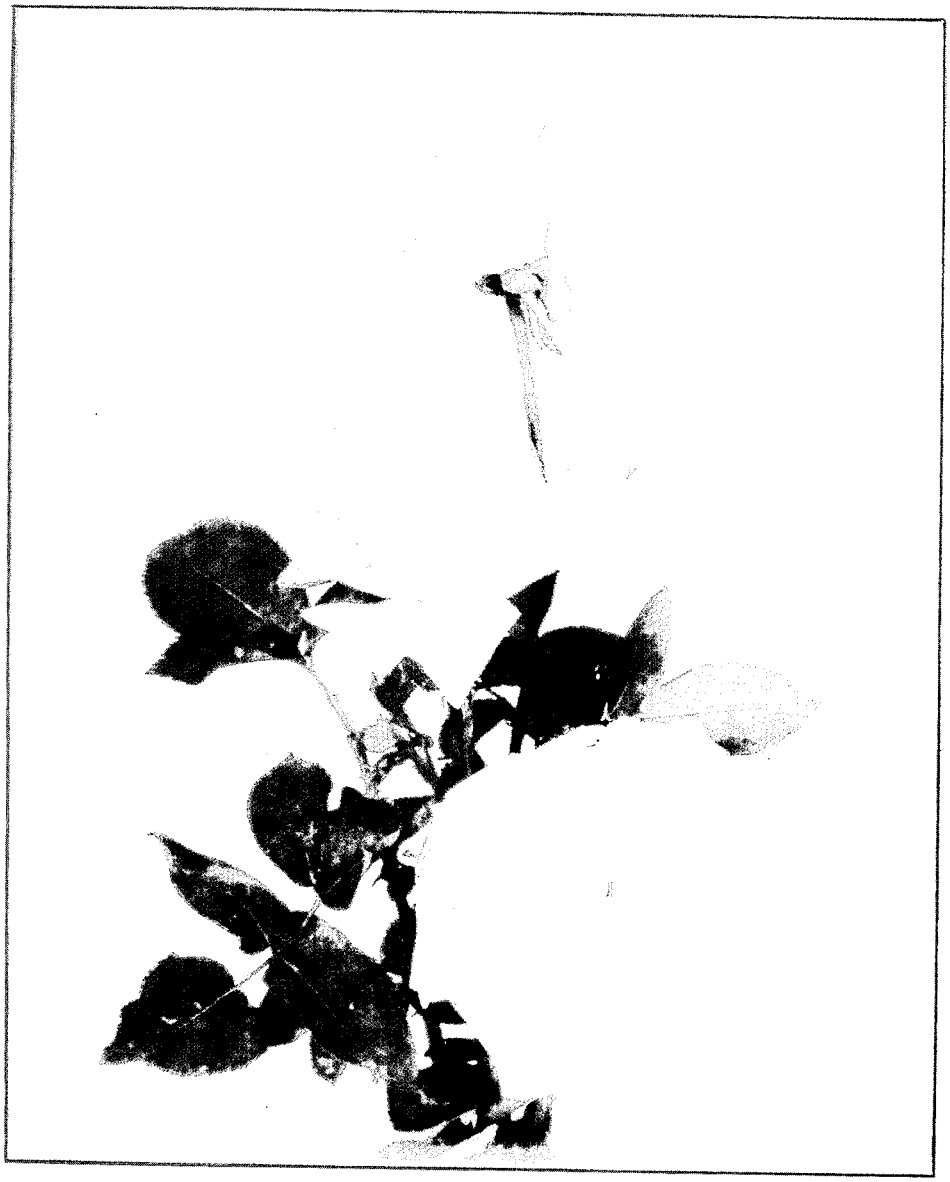
Inventor.
M. L. Whisler
By: Robb & Robb
Attorneys.

United States Patent Office

Plant Pat. 1,487

Patented June 19, 1956

1,487

ROSE PLANT

Milton L. Whisler, Granada Hills, Calif., assignor to Germain's, Inc., Van Nuys, Calif., a corporation of California Application October 21, 1955, Serial No. 542,124

1 Claim. (Cl. 47—61)

The present invention relates to a new and distinct variety of rose plant of the hybrid tea class, which was originated by me by crossing the variety "Charlotte Armstrong" (Plant Patent No. 455) with the variety "Katherine T. Marshall" (Plant Patent No. 607).

As the result of this breeding, I have produced a new and improved rose variety, the flowers of which have the general coloration and aspect of the variety "Dame Edith Helen" (unpatented), but which is particularly characterized as to novelty by its tall, upright and vigorous habits of growth, and large double flowers which are borne singly on exceptionally long and stiff cutting stems.

The foregoing characteristics and distinctions definitely differentiate my new variety from its parents, as well as from all other varieties of its class of which I am aware, and asexual reproduction of the new variety by budding, as performed by me at Saugus, California, shows that these distinctions and characteristics come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with the Horticultural Color Chart of the British Color Council, except where general color terms of ordinary dictionary significance are obvious:

Type: Half-hardy; tall; bush; outdoor; seedling; for cut flowers and for garden decoration.
Class: Hybrid tea.
Breeding: Seedling.
*Seed parent.*—"Charlotte Armstrong."
*Pollen parent.*—"Katherine T. Marshall."
Propagation: Holds its distinguishing characteristics through succeeding propagations by budding.

FLOWER

Locality where grown and observed: Saugus, California.
Flowers borne: Singly to stem; on strong, long stems.
Quantity of bloom: Free, outdoors.
Continuity: Continuous.
Fragrance: Moderate. Nature—Centifolia.
Bud:
*Peduncle.*—Long; heavy; stiff; almost smooth; with fed red hairs. Color—Scheeles Green, Plate 860/3.
*Before calyx breaks.*—Size—large. Form—globular; with foliaceous appendages on the surface of the bud; with slender, much-cut foliaceous parts extending beyond the tip of the bud equal to ½ of its length. Color—Scheeles Green, Plate 860/3.
*As calyx breaks.*—Color—Delft Rose, Plate 020.
*As first petal opens.*—Size—large. Form—long; ovoid. Color: outside—Delft Rose, Plate 020/3; inside—Spinel Pink, Plate 0625/1.
*Opening.*—Opens up well; is retarded from opening by cold weather.

Bloom:
*Size (when fully open).*—Large; from 5 inches to 6 inches.
*Petalage.*—Very double; usually with no stamens showing; from 45 to 50 petals; arranged irregularly.
*Form.*—Cupped at first, but becoming open-cupped; petals being at first tightly cupped, but later becoming loosely cupped and rolled outward at maturity.
Petals:
*Texture.*—Thin; soft; with inside satiny and outside shiny.
*Shape.*—Obovate.

This description of a newly opened flower was made from a rose grown outdoors in the month of June, at Saugus, California.

*Color.*—Outer petal: outside surface—Delft Rose, Plate 020/3; inside surface—Spinel Pink, Plate 0625/1. Intermediate petal; outside surface—Delft Rose, Plate 020/1; inside surface—Delft Rose, Plate 020/2. Inner petal: outside surface—Delft Rose, Plate 020/2; inside surface—Delft Rose, Plate 020/1.

This description was made from a rose that was open for 3 days outdoors in the month of June, at Saugus, California:

*Color.*—Outer petal: outside surface—Dawn Pink, Plate 523/2; inside surface—Dawn, Pink, Plate 523/2. Inner petal: outside surface—Rose Madder, Plate 23/3; inside surface—Rose Madder, Plate 23/2.
*General color effect.*—Newly opened flower—Camellia Rose, Plate 622/1. 3-days open—Neyron Rose, Plate 623/1.
*Behavior.*—Persist; does not open well in cool or damp weather.
*Flower longevity.*—On bush in garden—4 days in June. Cut roses grown outdoors and kept at living-room temperature—2 days in June.

REPRODUCTIVE ORGANS

Stamens: Many; arranged irregularly about pistils.
Filaments: Some medium length and some long; most with anthers. Color—Lemon Yellow, Plate 4/1.
Anthers: Medium size; all open at once. Color—Straw Yellow, Plate 604.
Pollen: Moderate. Color—Amber Yellow, Plate 505.
Pistils: Many.
Styles: Very short; very thin; bunched.
Stigma: Color—white.
Ovaries: Some protruding from calyx.
Hips: None.
Sepals: Permanent; long; recurved. Color (newly opened flower): outside surface—Scheeles Green, Plate 860/3; inside surface—Sage Green, Plate 000861/1.
Seeds: None.

PLANT

Foliage:
*Leaves.*—Compound of 7 leaflets; abundant; medium size; moderately heavy and leathery.
*Leaflets.*—Shape—ovate. Base—round. Margin—irregularly dentate.
*Color.*—Mature: upper surface—Ivy Green, Plate 000106/1; under surface—Spinach Green, Plate 0960/2. Young: upper surface—Fern Green, Plate 0862; under surface—basic color Lettuce Green, Plate 861, washed with Garnet Brown, Plate 00918/3.

*Rachis (the supporting stem of the compound leaf).*—Medium caliper. Upper side—grooved; hairy. Under side—moderately hairy and prickly.

*Stipules.*—Very short; narrow; with long points turning out at an angle of more than 45°.

*Disease resistance.*—Sometimes subject to mildew, but no blackspot has been observed, as compared with other varieties grown under comparable cultural conditions at Saugus, California.

Growth:

*Habit.*—Upright; much-branched.

*Growth.*—Vigorous.

*Canes.*—Medium caliper.

*Main stems.*—Color—Scheeles Green, Plate 860/1. Thorns — medium number; medium length; straight; with short, broad base. Color—medium cedar brown. Prickles—none. Hairs—none.

*Branches.*—Color—Scheeles Green, Plate 860/2. Thorns—from several to many; medium length; hooked downward; with broad base of medium length. Color—light cedar brown. Prickles—few. Color—very light tan. Hairs—few. Color—reddish brown.

*New shoots.*—Color—Scheeles Green, Plate 860/3, washed with Garnet Brown, Plate 00918/3. Thorns—many; long; hooked downward; with long, narrow base. Color—basic color Chrysanthemum Crimson, Plate 824/2, with white tips. Prickles—few. Color—Chrysanthemum Crimson, Plate 824/2. Hairs—few. Color—white.

1 claim:

A new and distinct variety of rose plant of the hybrid tea class, substantially as herein shown and described, characterized particularly as to novelty by its tall, upright and vigorous habits of growth, its habit of bearing flowers singly on exceptionally long and stiff cutting stems, and its large, double flowers having the general coloration and aspect of the variety "Dame Edith Helen" (unpatented).

No references cited.